(12) United States Patent
Dioguardi

(10) Patent No.: US 8,211,944 B2
(45) Date of Patent: *Jul. 3, 2012

(54) AMINO ACID BASED COMPOSITIONS FOR THE TREATMENT OF PATHOLOGICAL CONDITIONS DISTINGUISHED BY INSUFFICIENT MITOCHONDRIAL FUNCTION

(75) Inventor: Francesco Saverio Dioguardi, Milan (IT)

(73) Assignee: Professional Dietetics S.r.l., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/161,232

(22) Filed: Jun. 15, 2011

(65) Prior Publication Data

US 2011/0245312 A1    Oct. 6, 2011

Related U.S. Application Data

(63) Continuation of application No. 10/575,062, filed as application No. PCT/IB2004/003210 on Sep. 30, 2004, now Pat. No. 7,973,077.

(30) Foreign Application Priority Data

Oct. 7, 2003  (IT) ............................. TO2003A0789

(51) Int. Cl.
*A61K 31/195*    (2006.01)
(52) U.S. Cl. ...................................... 514/561
(58) Field of Classification Search .................. None
See application file for complete search history.

(56) References Cited

U.S. PATENT DOCUMENTS

| 3,764,703 A | 10/1973 | Bergstrom et al. |
| 5,026,721 A | 6/1991 | Dudrick et al. |
| 5,036,052 A | 7/1991 | Ozeki et al. |
| 5,719,133 A | 2/1998 | Schmidl et al. |
| 5,919,823 A | 7/1999 | Richardson |
| 6,218,420 B1 | 4/2001 | Dioguardi |
| 6,503,506 B1 | 1/2003 | Germano |
| 2004/0087490 A1 | 5/2004 | Troup et al. |
| 2004/0157903 A1 | 8/2004 | Conti et al. |
| 2004/0192756 A1 | 9/2004 | Conti et al. |

FOREIGN PATENT DOCUMENTS

| DE | 203 11 240 U1 | 9/2003 |
| EP | 0 341 895 A | 11/1989 |
| EP | 0 642 791 A1 | 3/1995 |
| WO | 95/22909 | 8/1995 |

OTHER PUBLICATIONS

Volpi et al. ("Essential amino acids are primarily responsible for the amino acid stimulation of muscle protein anabolism in healthy elderly adults," Am J Clinical Nutrition, 2003, 78, 250-258).*
Volpi et al., "Exogenous Amino Acids Stimulate Net Muscle Protein Synthesis in the Elderly," *J. Clin. Invest.*, 101:2000-2007 (1998).
Platell et al., "Branched-chain amino acids," *J Gastroenterology and Hepatology*, 15:706-717, abstract only (2000).
Naviaux R.K., "The Spectrum of Mitochondrial Disease," *Mitochondrial and Metabolic Disorders: A Primary Care Physician's Guide*, 2nd Ed.:3-10 (2003).
Marchesini et al., "Long-term oral branched-chain amino acid treatment in chronic hepatic encephalopathy," *Journal of Hepatology*, 11:92-101 (1990).
Forssell et al., "Early Stages of Late Onset Alzheimer's Disease," *Acta Neurol Scand*, 79(21):27-42 (1989).
International Search Report issued in PCT/IB2004/003210, mailed May 10, 2005.

\* cited by examiner

*Primary Examiner* — Christina Bradley
(74) *Attorney, Agent, or Firm* — Heslin Rothenberg Farley & Mesiti P.C.; Andrew K. Gonsalves

(57) ABSTRACT

The present invention relates to compositions suitable for the treatment of pathological conditions distinguished by insufficient or reduced mitochondrial function. The compositions comprise, as principal active ingredients, the amino acids leucine, isoleucine and valine. The compositions may also comprise, as further active ingredients, amino acids threonine and lysine, and optionally, histidine, phenylalanine, methionine, tryptophan, as well as tyrosine and cysteine.

9 Claims, No Drawings

AMINO ACID BASED COMPOSITIONS FOR THE TREATMENT OF PATHOLOGICAL CONDITIONS DISTINGUISHED BY INSUFFICIENT MITOCHONDRIAL FUNCTION

CROSS REFERENCE TO RELATED APPLICATIONS

This application is a continuation of U.S. patent application Ser. No. 10/575,062, filed Apr. 7, 2006, and published as US-2007/0010437 on Jan. 11, 2007, which is a 371 filing of PCT International Application No. PCT/IB2004/003210, filed Sep. 30, 2004, and published in English as WO 2005/034932 on Apr. 21, 2005, which claims the priority of Italian Application No. TO2003A000789, filed on Oct. 7, 2003, the disclosures of which are hereby incorporated by reference in their entirety.

The present invention relates to compositions for the treatment of pathological conditions distinguished by insufficient mitochondrial function.

Identification of specific pathologies of mitochondria date back some forty years, when a specific mitochondrial DNA was identified. However, it was only during the 1990's that a better knowledge of the synthesis, structure, and function of mitochondria was linked to specific clinical findings, and also to degenerative diseases correlated to age. Thanks to said knowledge there has been identified a series of primitive and secondary mitochondrial diseases, as well as the various target organs of mitochondrial lesions, such as the central nervous system (and hence Parkinson's disease, amyotrophic lateral sclerosis, Alzheimer's disease), the cardiovascular system in relation to ageing, skeletal muscles, micro-macroangiopathy, etcetera.

The therapeutic approaches deriving from said knowledge are still primitive and focus, above all, on the prevention of oxidative damage (Lufih R. and London B. R.—J. Intern. Med., 1995: 238, 405-421). In fact, the production of reactive oxygen species (ROS), which are the waste products of the oxidative metabolism, has been correlated to the progressive accumulation of damage to DNA and proteins at various levels in organs and cells, according to the so-called Harman hypothesis (Harman C. V.—Am. Geriatr. Soc., 1972: 20, 145-147), as well as to ageing. So far the therapeutic approaches have focused on anti-oxidant substances, such as N-acetyl-cysteine (Martins Bañaclocha M., Brain Res., 2000: 859, 173-175), glutathione (Viria et al., 1992 in: Free Radicals and Agents, 136-144, Birkhanserverlag, Basel), vitamin C (Ghosh M. K. et al., Free Radical Res., 1996: 25, 173-179), and carnitine (Hagen T. Metal, 1998, Proc. Math. Acad. Sci. USA, 95: 9562-9666). Some experimental results appear to confirm that the mean and maximum life of cell lines is favourably prolonged when the amounts of anti-oxidants are sufficient to eliminate the mitochondrial oxidative stress, restoring the metabolic activity of the mitochondria.

The present invention indicates the possibility of an absolutely innovative therapeutic approach to the aforesaid problem, based upon the use of specific amounts of given amino acids.

Three quarters of the total requirements of nitrogen are covered by just five amino acids: leucine, isoleucine, valine, threonine and lysine. This means that all the other amino acids, whether essential or non-essential, contained in dietary proteins, serve to cover only the remaining 25% of the nitrogen requirement of the organisms of mammals. In nature there do not exist proteins with a content of amino acids stoichiometrically similar to what is necessary for covering the requirement of nitrogen in human beings. This explains why an excessive intake of protein in food is a possible source of many medical problems: the intake of an excess of amino acids with respect to the ones necessary and usable will result in a functional overload of the mechanisms of elimination of waste and not in an improvement of the functions depending upon the availability of amino acids.

In the above perspective, amino acids can be compared to letters, and proteins to words. The syntheses are activated and proceed only in conditions where there is present an adequate quantity of all the necessary amino acids for the constitution of the entire final protein; otherwise, synthesis will not even start. Consequently, not only will the amino acids be necessary in the right qualities, but they will also be necessary in adequate quantities of each, like the letters for writing a given word. Take, for example, the Italian word "protein": to write it we need one p, one r, one o, one t, one i, one n, but two e's. The correct ratio between amino acids is not expressible in grams, but in terms of number of molecules, in the correct ratio between them, and in function of the concentration of amino acids present in the protein to be synthesized. As a result, the ratios are more correctly expressed as numbers of molecules, i.e., in gram-moles. This is the most precise way to express the ratio, said ratio being referred to properly as stoichiometric, between amino acids necessary for the synthesis of proteins.

A further level of complexity is due to the fact that synthesis of the proteins is an extremely expensive process from the energy standpoint; consequently, syntheses do not proceed unless there is an adequate availability of energy in the cell, and the energy is produced by the mitochondria. The production of energy is generally taken to depend upon anaerobic glycolysis of glucose and upon β-oxidation of free fatty acids (FFAs), which provide the two main substrates for maintenance of activity of the citric-acid cycle (aerobic glycolysis), a set of enzymes constituting the chief producer of the energy that enables us to live, which is oxygen-dependent. Deriving from anaerobic glycolysis is pyruvate, and from this, by carboxylation, oxaloacetate, or, by decarboxylation, acetylCoA, which, by condensing with one another, give rise to the citrate necessary for maintenance of the activity of the cycle. AcetylCoA can derive also from β-oxidation, or from the metabolism of some amino acids, which are consequently called «ketogenetic amino acids», whilst pyruvate, citrate and oxaloacetate can also be derived from the metabolism of other amino acids, referred to as «glucogenetic amino acids» because the liver can synthesise glucose from these molecules. The use of substrates derived from amino acids or FFAs enables a saving in the consumption of glucose. Glycaemia, outside of the period in which the absorption of food enables an increase in the glucose of exogenous origin in the blood, is maintained by the liver, with the release of glucose from the reserve deposit, i.e., glycogen, and with the continuous neo-synthesis of glucose starting from specific amino acids (neoglucogenesis). Glycogenolysis and neoglucogenesis are always simultaneously active in the post-absorption period, albeit in different ratios (just as is glycogenogenesis, in part fed by neoglucogenesis). Cells, tissues and organs, as well as the body itself, are open systems, in which it is necessary, and hence possible, to identify an input of information, material and energy.

On the basis of these general biochemical premises, the inventor has hypothesized that the availability of specific amino acids is able to transmit to the cells a dual message: on the one hand, the availability of plastic material, on the other, the availability of energetic material. The inventor has moreover hypothesized that a specific degree of availability, if adequately coupled to the duration and constancy of the variations of concentration, constitutes a mediator to cells of the information that there exists an adequate availability of material and energy for activating the renewal or development of intracellular structures. Consequently, for cells in which this is possible, it is useful, or necessary, to activate cell duplication itself.

There do not exist similar hypotheses on the properties of control of the cell response that an adequate input is potentially able to provide.

The consequences of this approach are interesting: there exists the possibility of identifying an energetic-metabolic lowest common denominator that is able to maximize the response of cells, identifying kinds and quantities of a mixture of amino acids capable of supplying the right message to given tissues and organs, or to the entire body. The levels of response will presumably be different within the cells, and hence within the tissues, the organs, and the body as a whole. The corollary to this hypothesis is the question: what may be, within the cells, the structures capable of receiving messages from the environment, and of transmitting to the cell, and from the cell to the tissue, and so on with increasingly greater complexity, the message that it is possible to set under way new syntheses, or to employ sufficient, but huge, energy and plastic resources in new cells.

The attention of the inventor has thus been centred on the key organelle in the production of energy, namely, the mitochondrion. A series of recent studies has shown that the survival of the cells and the very duration of the life of cells, depends upon the mitochondrion. The presence of oxidants (ROS) produced by metabolism shortens the life of the mitochondrion and of the cells. A recent study has moreover shown that, in dilative myocardiopathy, the mitochondria that are closest to the outside of the cells are less sensitive to the oxidative insults towards the surface (and that hence the syntheses proceed in an eccentric way), beneath the sarcolemma, than those towards the centre of the cells, where the mitochondria are more readily liable to undergo apoptosis (Fannin S. W. et al., Arch. Biochem. Biophys., 1999: 372, 399-407). Apoptosis itself, via caspase cascade, can be triggered by the mitochondria (Dirks A. and Leeuwenburg C., Am. J. Physiol. Regulatory Integrative Comp. Physiol., 2002: 282, R519-527).

As has been said, three quarters of the nitrogen requirement of the organism are covered by five essential amino acids. Four of these are neutral amino acids, of which three are branched chain amino acids: leucine (ketogenetic), isoleucine (ketogenetic and glucogenetic), valine (glycogenic), and threonine (glycogenic), characterized by a hydroxyl group in position β; the fifth is a basic amino acid, lysine, which has an amine group ($NH_3'$) in position ε.

Starting from the premises set forth above, the studies underlying the present invention have enabled identification of a stoichiometric mixture of amino acids that would enable maximum use for synthetic purposes, optimizing, at the same time, coverage of the energy requirement of the mitochondrial energy metabolism. According to the invention:

1) the mixture envisages the use of the branched amino acid leucine in combination with at least one between, and preferably both of, the branched amino acids isoleucine and valine. The ratios, expressed in gram-moles between the amino acids, in proportion to 1 gram-mole of L-Leucine, can be identified as follows:

L-Isoleucine: from 0.2 to 0.7, preferably from 0.4 to 0.6;
L-Valine: from 0.2 to 0.7, preferably from 0.4 to 0.6.

2) The mixture envisages, as further active ingredients, at least one between, and possibly both of, the amino acids threonine and lysine. The ratios, expressed in gram-moles between the amino acids, in proportion to 1 gram-mole of L-Leucine, can be identified as follows:

L-Threonine: from 0.15 to 0.50, preferably from 0.2 to 0.45;
L-Lysine: from 0.15 to 0.60, preferably from 0.3 to 0.55.

At the current state of the studies conducted by the inventor, the formulation that appears to present a greater degree of activity is a formulation in which, setting at 1 the sum of leucine, isoleucine and valine, in the reciprocal dimensions based upon the gram molecular weight identified in point 1), the sum of threonine and lysine is between 10% and 50% of said formulation (always on the basis of the gram molecular weight of the substances in question), and preferably between 25% and 45%.

3) The nutritional intake of the mixture can be integrated with one or more further essential amino acids, and in particular histidine, methionine, phenylalanine, tryptophan. Setting at 1 the sum of leucine, isoleucine, valine, threonine and lysine, the other essential amino acids (histidine, methionine, phenylalanine, tryptophan) are represented in a global amount (again expressed as gram molecular weight/gram molecular weight ratios) ranging from 2% to 25%, and preferably from 5% to 15%.

4) Two non-essential amino acids can possibly optimize the mixture of the aforesaid amino acids by addition thereto:

4.1) tyrosine (which is physiologically produced by hydroxylation of phenylalanine), since derivation of tyrosine from phenylalanine can occur only in the liver, whilst an important use occurs peripherally, for example, in muscle or in the myocardium, where the enzymatic route for hydroxylation of said amino acid does not exist; the optimal amount of tyrosine has been identified as one ranging from 15% to 50% of the amount of phenylalanine present in the mother mixture, and preferably from 20% to 35%. The greater the hepatic impairment, or the peripheral requirement as a function of a reduced intake from other sources, the greater will be the usefulness of increasing the stoichiometric ratios between tyrosine and phenylalanine, up to an indicative maximum of 50%;

4.2) cyst(e)ine (cystine and/or cysteine), which will preferably be at least 100%, with an optimal amount identified as being comprised between 150% and 350%, of the amount of methionine present in the mother mixture.

The aforesaid presence of cysteine, which can be readily transformed metabolically into methionine, will prevent the relative shortage of cysteine, in the process of interconversion of methionine into cysteine, from giving rise, in conditions of relative excess of methionine or shortages of folates, to the toxic intermediate, i.e., homocysteine, and stopping at that point.

5) One or more other amino acids may be envisaged as further active ingredients of the mixture, the sum in gram molecular weight of which will be in a percentage lower than 20% with respect to the other active ingredients, and less than 10% for each individual additional amino acid.

6) In its preferred formulation, the mixture according to the invention has a pH in aqueous solution of between 6.5 and 8.5, whether with or without excipients suitable for the preparation of tablets, capsules, powders, etc., and in any pharmacological form of presentation suitable for enteral or parenteral use.

Further specifications, in terms of amounts and ratios between the various amino acids envisaged by the compositions according to the invention, are contained in the attached claims, which constitute an integral part of the present description. Even though the ratios are expressed on the basis of molecular weight, the ones indicated in the attached claims are applicable, in general terms, also in the case of calculation based on the weight in grams of the various amino acids indicated (bearing, however, in mind that the amount of lysine, expressed in grams rather than in moles, may then be greater than the individual amounts of isoleucine and valine).

An example of formulation of the mixture of amino acids according to the invention, made in accordance with the principles indicated, is given in the following table:

TABLE 1

| Amino acid | Molec. Weight* | g/100 g | % of total | % of cluster |
|---|---|---|---|---|
| L-Leucine | 131.17 | 31.2500 | 31.25% | 50.00% |
| L-Isoleucine | 131.17 | 15.6250 | 15.63% | 25.00% |
| L-Valine | 117.15 | 15.6250 | 15.63% | 25.00% |
| Totals - Cluster A | | 62.5000 | 62.50% | 100.00% |
| L-Lysine | 146.19 | 16.2500 | 16.25% | 65.00% |
| L-Threonine | 119.12 | 8.7500 | 8.75% | 35.00% |
| Totals - Cluster B | | 25.0000 | 25.00% | 100.00% |
| L-Histidine | 155.16 | 3.7500 | 3.75% | 46.88% |
| L-Phenylalanine | 165.19 | 2.5000 | 2.50% | 31.25% |
| L-Methionine | 149.21 | 1.2500 | 1.25% | 15.63% |
| L-Tryptophan | 204.23 | 0.5000 | 0.50% | 6.25% |
| Totals - Cluster C | | 8.0000 | 8.00% | 100.00% |
| L-Tyrosine | 181.19 | 0.7500 | 0.75% | |
| L-Cystine | 240.30 | 3.7500 | 3.75% | |
| Totals for composition | | 100.0000 | 100.00% | |

*from «Amino Acids, Nucleic Acids & Related Compounds - Specification/General Tests», $8^{th}$ Edition, Kyowa Hakko Kogyo Co., Ltd.

In the following table, the amount in grams of the composition referred to in Table 1 are expressed on the basis of molecular weight.

TABLE 2

| Amino acid | Molec. Weight | moles | % of total | % of cluster |
|---|---|---|---|---|
| L-Leucine | 131.17 | 0.23824 | 31.97% | 48.55% |
| L-Isoleucine | 131.17 | 0.11912 | 15.98% | 24.27% |
| L-Valine | 117.15 | 0.13338 | 17.90% | 27.18% |
| Totals - Cluster A | | 0.49074 | 65.85% | 100.00% |
| L-Lysine | 146.19 | 0.11116 | 14.92% | 60.21% |
| L-Threonine | 119.12 | 0.07346 | 9.86% | 39.79% |
| Totals - Cluster B | | 0.18461 | 24.77% | 100.00% |
| L-Histidine | 155.16 | 0.02417 | 3.24% | 48.21% |
| L-Phenylalanine | 165.19 | 0.01513 | 2.03% | 30.19% |
| L-Methionine | 149.21 | 0.00838 | 1.12% | 16.71% |
| L-Tryptophan | 204.23 | 0.00245 | 0.33% | 4.88% |
| Totals - Cluster C | | 0.05013 | 6.73% | 100.00% |
| L-Tyrosine | 181.19 | 0.00414 | 0.56% | |
| L-Cystine | 240.30 | 0.01561 | 2.09% | |
| Totals for composition | | 0.74522 | 100.00% | |

As will emerge clearly hereinafter, the administration of a mixture according to the invention, and in particular according to Table 1, is decisive in increasing the number of mitochondria. On the one hand, this leads to an inhibition of apoptosis, via a precise caspase-mediated mechanism, which is the inhibition of activation of the caspase specifically resulting from mitochondrial suffering; on the other hand, it leads to an increase in the availability of energy for each individual cell, and hence to the clinical improvement referred to.

The mixture is functional for achieving this result by virtue of peculiar stoichiometric ratios between "clusters" of amino acids, which can be inferred also from Table 2. It should be noted that these are not necessarily chemico-physical "clusters", nor do they have any other common metabolic characteristics except for the final result at which the peculiar stoichiometric ratios aim: covering the energy requirements, and in any case allowing availability of amino-acid substrate for the necessary processes of synthesis. It is the simultaneous availability for satisfying both of these needs which actuates the anti-apoptosis and synthetic command.

Clinical Studies

The problem was approached in two different ways, i.e., from the clinical standpoint and from the experimental standpoint, proceeding in a logical sequence.

In the knowledge that in the elderly there occurs a reduction in the number of mitochondria in the muscular structure or mass, a clinical study was conducted to verify whether the beneficial effects of supplementing with the mixture according to Table 1 could be confirmed in elderly subjects with problems of limitation of mobility. In this type of patients, a reduced mobility creates disability in movement, causing loss of muscular trophism, and this in turn, in a vicious circle, brings about a further reduction of mobility. In these patients, the incapacity to adapt their cardiac function to the greater workload required by physical activity can become one of the limiting factors.

There were consequently enrolled 40 patients aged over 65 years, who led a sedentary life and suffered from a low quality of life in relation to their state of health, with a normal ventricular ejection (VE) at rest, without angina, or any other invalidating pathological condition. Their reduced physical activity was documented by a 6-minute walking test, and their perception of difficulty of deambulation via a questionnaire on invalidity in walking. In addition, using a dynamometer, the maximum isometric muscular force was measured. VE was moreover measured at rest and during isometric exercise with two-dimensional echocardiography. The data were evaluated prior to and at the end of 3 months of oral administration of the mixture of amino acids according to Table 1.

Body Mass Index (BMI) was not modified by the therapy, but the distance covered in a 6-minute walk increased from 214.5±32 metres to 262.8±34.8 metres (P<0.001) after the treatment, and there was likewise an improvement in the data of the self-assessment questionnaire, as regards distance, speed and number of flights of stairs (P<0.001, with respect to the basal values). VE at rest (normal: >50%) was not modified by the therapy, nor was blood pressure or heart rate.

The capacity for isometric exercise measured with a dynamometer (handgrip test), instead, increased from 16.6±2.4 to 19.2±2.2 (P<0.001). Under stress, VE should not vary or increase in normal conditions, by more than 0.05 U. Prior to start of therapy, 66% of the patients showed a decline in VE under stress (P>0.005), whilst the remaining 34% had a normal response. In 93% (P<0.001) of the patients with altered VE, after three months of therapy, VE under stress increased or remained unchanged with respect to the basal value, i.e., it had normalized.

Various experimental models were adopted to interpret and explain the mechanism through which the aforesaid mixture of amino acids were able to activate a better energetic performance of the muscular cells of the myocardium in the clinical study described.

A first experimental model, using the perfused isolated heart of a rat, furnished indirect indications, which enabled confirmation of the hypothesis that the mitochondrion was the organelle to be studied as possible actor in the attainment of the results found. For this purpose, in the isolated heart of a rat, perfused with a standard buffer solution, a perfusion phase of 30 minutes was followed by a phase of complete ischaemia (ligation of the coronaries) and asystolia protracted for 30 minutes; then, the myocardium was re-perfused and made to start beating again.

The groups were three:
a) a control group;
b) a group similar to the controls, but with an acute perfusion with the mixture referred to in Table 1, in an amount of 0.25 mg/mL in the phase of 30 minutes that preceded ischaemia and in that of post-ischaemic re-perfusion;
c) a group of animals treated for 20 days with 1 g/kg/d of the mixture referred to in Table 1, prior to isolation of the myocardium.

The variables measured were:
systolic and diastolic arterial pressure (PA);
release of creatinphosphokinase (CPK) and lactate (enzymatic tests);
mitochondrial activity (with Clark's electrode);
apoptosis of endothelial cells and of cardiomyocytes (with TUNEL);
the activity of caspase-3 and caspase-9 in the endothelium and in the cardiomyocytes (with the fluorimetric test).

The results can thus be summed up as described in what follows.

Group ≦a≧ (controls) and group ≦b≧ (acute perfusion in an untreated animal) showed results altogether similar for all the parameters examined, and hence no effect. Instead, the hearts of animals of group ≦c≧ (pre-treated for 20 days with 1 g/kg/d of the mixture referred to in Table 1 prior to isolation of the myocardium) presented a clearly lower diastolic arterial pressure (PA), as well as a functional response to re-perfusion and a clearly higher recovery of ventricular contraction.

Likewise, there was a significant reduction in the release of CPK, which indicates a greater integrity of the cell membranes, and in the release of lactate, said reduction indicating a greater use of pyruvate by the citric-acid cycle, albeit in total absence of oxygen, since it was no longer arriving with the blood.

At this point, a check was made to see whether there was any increase in the production of energy, and how this could influence myocardial contractility during a protracted ischaemic phase, and in the re-perfusion phase.

Using the same methodology, and the same treatment groups, there was then studied the content of ATP and creatine phosphate (CF) in the tissue, as well as mitochondrial activity, evaluating the $VO_2$ and the production of mitochondrial ATP.

Only the chronic treatment (group «c»: 1 g/kg/d of the mixture referred to in Table 1 prior to isolation of the myocardium) gave rise to statistically significant modifications of the parameters examined, inducing an improvement, i.e., increase, in the activity of the mitochondria.

Since the integrity of the mitochondria is fundamental for the maintenance of the integrity of living cells, it was of particular interest to identify whether the mixture referred to in Table 1 had an effect on apoptosis, and in order to understand the possible mechanisms of control different levels of cascade of caspases, i.e., the enzymatic mechanisms controlling intracellular apoptosis, were studied.

Since the mitochondrion is the organelle that produces energy, it is fundamental for the life of the cell. The loss of mitochondria will result in a progressive loss of the energy assets of the cell, with progressive impairment of the processes of elimination of waste material, of synthesis, and of cell function. The cell becomes less and less able to maintain itself; consequently, the process of apoptosis (a form of cell suicide) takes place to reduce the number of inefficient cells and to give to the others the possibility of replacing them or of surviving in conditions of lower competition on the substrates. Apoptosis is controlled by various mechanisms, some of which are extracellular, for activation of specific receptors, and some of which are intracellular, of which the principal one—which is perhaps indispensable post-receptor mediator also for the others—is under mitochondrial control. Apoptosis of mitochondria releases cytochrome c into the cytoplasm, and this activates caspase-9, which is followed by direct activation of the remaining apoptotic cascade.

This notation is of particular importance for an understanding of the mechanism of action of different therapeutic approaches on apoptosis: the control of the mitochondrion on caspase-9 is specific and, hence, in order to be certain not to have created random events or possible interference with other mechanisms of activation of different caspases, also caspase-8 was studied (activation of which is principally linked to IL-1 and to TNFα).

Caspase-9 (dosed in a blind way by an external laboratory) was the only one to show a significant reduction in its presence in the animals of group «c», which were treated chronically via oral route for 20 days, with 1 g/kg/d of the mixture referred to in Table 1 prior to isolation of the myocardium. No modification was observed in the study of caspase-8, activated by membrane receptors.

This series of studies makes it possible to understand how the results observed experimentally and in the clinical study in humans referred to previously is necessarily to be ascribed to the mitochondrion, independently of receptor activation and extracellular influences.

Finally, then, it was verified whether the greater cellular metabolic efficiency was due to an increased activity of individual mitochondria or else—and this is an event known to be indispensable during cell duplication, being historically well documented and filmed in experimental observations (Padoa E. 1967, in: Biologia Generale, 3rd edition. Chapter 4: La cellula, 116-189, Boringhieri Editore S.p.A., Turin), but never even hypothesized as being inducible in physiological or pathological conditions—whether the mitochondria were multiplied, increasing their number, in response to the introduction of the mixture of amino acids according to the invention.

This led to the need to count the number of mitochondria, before and after treatment, in pathological conditions that reduced the number thereof, and similar to those in which the study in humans had been conducted.

Eighteen-month old Wistar rats were taken, checked at 22 and 24 months. A control group was compared to a group that was treated with the mixture of amino acids according to the invention, adopting a randomization criterion. First of all, the number of mitochondria (MT) was counted independently, using histochemical and ultrastructural methods (by electronic microscopy) in six-month old animals, as controls. The number of the mitochondria in the peripheral muscle, in the myocardium, and in the cells of the cerebral cortex, was proportionally reduced according to age (i.e., a smaller number in the older animals).

Administration of the mixture referred to in Table 1 of 0.3 $g/kg/d^{-1}$ to the senescent animals proved extremely efficient in maintaining the patrimony of mitochondria more intact, i.e., higher, by a percentage value of 26±5% and 31±17%, respectively, than for the untreated animals of comparable age in the checks carried out at 22 months and at 24 months.

From this it is shown that increasing the number of mitochondria is not only possible but certainly therapeutic in various conditions.

Subsequent analyses enabled ascertainment of the fact that an improvement of 23±14% in the number of mitochondria was possible with just five amino acids of the mixture of Table 1, using a stoichiometric ratio of approximately 1:0.5 between the sum of leucine, isoleucine and valine (1), and the sum of threonine and lysine (0.5). With the removal of threonine and/or lysine, the number of mitochondria was not modified significantly in any of the animals. The reduction of leucine to below 15% of the total weight of the mixture led to nullifying significantly the positive effects of the mixture, whilst the effects were less marked, albeit statistically significant, if just isoleucine or just valine were reduced in the same proportion from the mixture, provided that the leucine was maintained constant (in said perspective, the compositions according to the invention may envisage up to 60% of leucine but not less than 15% with respect to the other two branched amino acids, up to 40% of isoleucine, but not less than 15% with respect to the other two branched amino acids, and up to 40% of valine, but not less than 15% with respect to the other two branched amino acids).

The preliminary studies carried out, in which different types of conditions regarding nutritional intake, and to the amount of physical exercise imposed, enabled confirmation of how, in volunteers, the stoichiometric ratios as claimed between the different amino acids take into account the most extreme needs, minimizing the possibility of an individual amino acid being found in excess, or deficient, in the reciprocal ratio with the others, and that said ratios enable maximum use of the amino acids for, synthetic purposes, optimizing, at the same time, the coverage of the energy requirements of the mitochondrial energy metabolism.

From the foregoing, it emerges clearly how the compositions according to the invention prove useful for the treatment of pathological conditions distinguished by insufficient mitochondrial function in humans and in animals, such as sarcopenia of the aged and senescence, in so far as they are designed to maintain intact and/or restore and/or increase the number of intracellular mitochondria, as well as to modify in a positive sense the activity of production of intracellular energy. The compositions according to the invention thus prove useful in every condition in which a reintegration of a reduced cellular energetic activity may modify to advantage the activity of the cell itself, and hence of the tissue and organ that is formed by the set of cells, such as an increase of neuronal activity in degenerative diseases of the nervous system (Alzheimer's disease, amyotrophic lateral sclerosis, Parkinson's disease), in which the activity of the cells decreases on account of reduced energy capacity, which involves a loss of the mitochondrial energetic activity. Likewise, the compositions according to the invention are suitable for use in every condition in which ischaemic states of any aetiology inhibit the energetic activity of the cell, promoting the maintenance of the structures designed to produce energy, and in particular the integrity of the mitochondria. The compositions also prove advantageous in every condition in which it is useful to the function of the organ to antagonize the apoptotic phenomena of the mitochondria and controlled by the mitochondria, which are not linked to apoptosis mediated by cell-membrane receptors and by means of other caspases that are not the ones activated by caspase-9.

The field of application of the invention extends to proteins obtained from genetic engineering or any other artificial method, in which there is a stoichiometric composition of amino acids as described above and claimed in the annexed claims.

In order to implement the invention, the amino acids indicated above can be replaced by respective pharmaceutically acceptable derivatives, namely salts.

The invention claimed is:

1. A method for treating sarcopenia of an elderly subject, said method comprising:
    administering via oral route to the elderly subject a therapeutically effective amount of a composition comprising, as active ingredients, the following:
    (i) the branched chain amino acids leucine, isoleucine, and valine, and/or salts thereof;
    (ii) lysine and threonine, or salts thereof; and
    (iii) other essential amino acids selected from: histidine, methionine, phenylalanine, and tryptophan, or salts thereof, wherein
    the amount in moles of threonine is smaller than the individual amounts of lysine and of said branched amino acids, or salts thereof, but greater than the sum of the individual amounts in moles of said other essential amino acids, or salts thereof; and
    the amount in moles of lysine is smaller than the individual amounts of said branched amino acids, or salts thereof, but greater than the sum of the individual amounts in moles of said other essential amino acids, or salts thereof,
    wherein isoleucine, valine, threonine, and lysine are present in the following molar ratios to leucine:
    isoleucine/leucine having a molar ratio from 0.2 to 0.7;
    valine/leucine having a molar ratio from 0.2 to 0.7;
    threonine/leucine having a molar ratio from 0.15 to 0.50; and
    lysine/leucine having a molar ratio from 0.15 to 0.60.

2. The method according to claim 1, wherein the sum of the amounts in moles of histidine, methionine, phenylalanine, tryptophan, or salts thereof, is from 2% to 25% of the sum of the amount in moles of leucine, isoleucine, valine, lysine, and threonine, or salts thereof.

3. The method according to claim 1, wherein the composition further comprises, as an active ingredient, at least one of tyrosine and cyst(e)ine, or salts thereof.

4. The method according to claim 1, wherein the composition further comprises tyrosine or a salt thereof, and wherein the amount in moles of tyrosine or salt thereof is from 15% to 50% of the amount in moles of phenylalanine or salt thereof.

5. The method according to claim 1, wherein the composition further comprises cyst(e)ine or a salt thereof, and wherein the amount in moles of cyst(e)ine or salt thereof is at least equal to 100% of the amount in moles of methionine or salt thereof.

6. The method according to claim 3, wherein the composition further comprises both tyrosine and cyst(e)ine.

7. The method according to claim 2, wherein the sum of the individual amounts in moles of threonine and lysine, or salts thereof, is smaller than the sum of the individual amounts in moles of said branched amino acids, or salts thereof, but greater than the sum of the individual amounts in moles of the said other essential amino acids, or salts thereof.

8. The method according to claim 2, wherein the amount in moles of threonine, or salt thereof, is smaller than the individual amounts in moles of lysine and of said branched amino acids, or salts thereof, but greater than the individual amounts in moles of said other essential amino acids, or salts thereof.

9. The method according to claim 2, wherein the amount in moles of lysine, or salt thereof, is smaller than individual amounts in moles of said branched amino acids, or salts thereof, but greater than the individual amounts in moles of said other essential amino acids, or salts thereof.

* * * * *